United States Patent [19]

Kusy et al.

[11] Patent Number: 5,403,895
[45] Date of Patent: Apr. 4, 1995

[54] SYNTHESIS OF AMINATED PVCS BY CONTROLLED REACTION WITH PIPERAZINE

[75] Inventors: Robert P. Kusy; Vasile V. Cosofret; John Q. Whitley; Erno Lindner; Richard P. Buck, all of Chapel Hill, N.C.

[73] Assignee: The University of North Carolina at Chapel Hill, Chapel Hill, N.C.

[21] Appl. No.: 44,295

[22] Filed: Apr. 7, 1993

[51] Int. Cl.[6] .............................................. C08F 8/30
[52] U.S. Cl. .............................. 525/326.2; 525/331.1; 525/331.3; 525/331.5
[58] Field of Search ............... 525/326.2, 331.1, 331.3, 525/331.5

[56] References Cited

U.S. PATENT DOCUMENTS

| | | | |
|---|---|---|---|
| 1,616,994 | 2/1927 | Sebrell . | |
| 2,972,586 | 2/1961 | van der Neut et al. | 260/2.1 |
| 3,063,882 | 11/1962 | Cheshire | 525/331.5 |
| 3,104,235 | 9/1963 | Kuntz et al. | 260/41.5 |
| 3,232,914 | 2/1966 | Pedersen | 260/87.5 |
| 3,410,811 | 11/1968 | Bufton et al. | 260/2.1 |
| 3,441,545 | 4/1969 | Blatz et al. | 525/331.5 |
| 3,511,898 | 5/1970 | Dekking | 260/885 |
| 3,621,085 | 12/1971 | Ichikawa | 264/2 |
| 3,647,774 | 3/1972 | Webb et al. | 260/94.2 |
| 3,671,511 | 6/1972 | Honnen et al. | 260/93.7 |
| 3,835,011 | 9/1974 | Baum et al. | 204/195 |
| 3,843,505 | 10/1974 | Higuchi | 204/195 |
| 3,884,846 | 5/1975 | Otsuki et al. | 260/2.2 |
| 3,953,348 | 4/1976 | Lee | 252/51 |
| 4,136,136 | 1/1979 | Dreyfuss et al. | 260/878 |
| 4,277,566 | 7/1981 | Kataoka et al. | 521/32 |
| 4,388,165 | 6/1983 | Koshiishi et al. | 204/418 |
| 4,761,233 | 8/1988 | Linder et al. | 210/500.37 |
| 4,774,294 | 9/1988 | Gurgiolo et al. | 525/331.5 |
| 4,814,060 | 3/1989 | Banks | 204/406 |
| 4,853,440 | 8/1989 | Roggero et al. | 525/338 |
| 4,904,742 | 2/1990 | Perichaud et al. | 525/331.4 |
| 4,913,816 | 4/1990 | Waite | 210/490 |
| 4,992,176 | 2/1991 | Bartels | 210/640 |
| 5,102,527 | 4/1992 | Shibata et al. | 204/416 |
| 5,112,491 | 5/1992 | Strantz, Jr. | 210/651 |
| 5,126,504 | 5/1992 | Bartels | 585/818 |

FOREIGN PATENT DOCUMENTS

| | | |
|---|---|---|
| 320023A | 6/1989 | European Pat. Off. . |
| 6105705 | 8/1981 | Japan . |
| 7027101 | 2/1982 | Japan . |
| 8142905 | 8/1983 | Japan . |

OTHER PUBLICATIONS

Cosofret et al. "Design of ionophore-free H[+]-selective solvent polymeric membranes for further biomedical applications": J. Electroana. Chem., 345 (1993) 169-181.
Linder et al. "Flexible (Kapton-based) Microsensor Arrays of High Stability for Cardiovascular Applications" J. Chem. Soc. Faraday, Trans 1993, 89(2), 361-367.
Meyerhoff et al. "New Anion and Gas-Selective Potentiometric Sensors", Chemical Sensors and Microinstrumentation Symposium, (Sep., 1988).
Buerk, Donald G., Biosensors, Theory and Applications, Ch. 3, pp. 39-45.
Cha et al. "Electrochemical Performance, Biocompatibility, and Adhesion of New Polymer Matrices for Solid-State Ion Sensors", Analytical Chemistry, vol. 63, No. 17 (Sep. 1991) pp. 1666-1672.
Cragg et al. Journal of Chemical Education, "PVC Matrix Membrane Ion-Selective Electrodes", vol. 51, No. 8, (1974) pp. 541-544.
Ma et al. "Potentiometric pH Response of Membranes Prepared with Various Aminated-Poly(vinyl Chloride) Products", Mikrochim, Acta, pp. 197-208 (1990).
Ma et al. "Response Properties of Ion-Selective Polymeric Membrane Electrodes Prepared with Aminated and Carboxylated Poly(vinyl chloride)", Analytical Chemistry, vol. 60, No. 20, (Oct. 1988) pp. 2293-2299.
Moody et al., "A Calcium-sensitive Electrode Based on a Liquid Ion Exchangers in a Poly(vinyl chloride) Matrix", Analyst vol. 95, pp. 910-918 (Nov. 1970).

Primary Examiner—Bernard Lipman
Attorney, Agent, or Firm—Richard F. Jenkins

[57] ABSTRACT

Disclosed are a copolymer composition comprising a substituted halo-polymer wherein from about 0.01% to about by weight of the halo moieties therein are replaced with piperazine, and a flexible plastic film made from the copolymer. The copolymer is inherently conductive.

12 Claims, No Drawings

SYNTHESIS OF AMINATED PVCS BY CONTROLLED REACTION WITH PIPERAZINE

TECHNICAL FIELD

This invention, in general, relates to halogenated polymers wherein some of the halo moieties are substituted by amine moieties. More particularly, this invention relates to such aminated halo-polymers wherein the amine moieties comprise piperazine. Even more particularly, this invention relates to novel aminated polyvinyl chloride (hereinafter aminated PVC) wherein the amine comprises piperazine, namely PVC-piperazine copolymers.

BACKGROUND OF THE INVENTION

PVC aminated with certain mono-amines and di-amines is shown in Ma, Chaniotakis, and Meyerhoff, "Response Properties of Ion-Selective Polymeric Membrane Electrodes Prepared With Aminated and Carboxylated Poly(Vinyl Chloride)", *Analytical Chemistry*, Vol. 60, No. 20, pp. 293–2299 (Oct. 15, 1988), and in Ma and Meyerhoff, "Potentiometric pH Response of Membranes Prepared With Various Aminated-Poly(Vinyl Chloride) Products", *Mikrochimica Acta*, Vol. I, pp. 197–208 (1990). For instance, an amine such as diaminoethane or octadecylamine is refluxed with PVC and the resultant aminated PVC is used to prepare pH-selective membranes for sensor construction. Although both Ma et al. articles indicate that the membranes exhibited Nernstian potentiometric pH responses over different pH ranges, it is noted that the potentiometric pH response alleged by Ma et al. could not be repeated, as set out in Example III below.

Gugiolo et al. U.S. Pat. No. 4,774,294 (Sep.27, 1988), assigned to Dow Chemical Company, show an electromagnetically-shielded body having an electroconductive film. The film is made by using certain amines in order to dehalogenate halo-polymers; for instance, diethylenetriamine (hereinafter DETA) is used to dechlorinate polyvinylidene chloride (hereinafter PVDC) film, and the dechlorinated PVDC film is glued with epoxy to a polyethylene film. The resultant is antistatic in that it dissipated 5000 volts in less than milliseconds (the accepted military specification).

Otsuki et al. U.S. Pat. No. 3,884,846 (May 20, 1975), assigned to Toyo Soda Manufacturing Company, show a process for removing heavy metals from a solution (i.e., water contaminated with heavy metals) by complexing the metal with a partially dehydrochlorinated PVC in the presence of an amine and a thio-compound.

Lee U.S. Pat. No. 3,953,348 (Apr. 27, 1976), assigned to Standard Oil Company, discloses additives for use as lubricants in automobile engines. The additives are formed by first reacting a high molecular weight polyolefin with acetonitrile and a halogen to form an intermediate, and then reacting the intermediate with N,N'-bis(aminoalkyl) piperazine.

Some general background showing use of PVC in membranes is disclosed in Waite U.S. Pat. No. 4,913,816 (Apr. 3, 1990), assigned to Ionics Incorporated, and Banks U.S. Pat. No. 4,814,060 (Mar. 21, 1989), assigned to Nalco Chemical Company. The '816 patent discloses a thin film membrane comprising a microporous support layer coated by a thin polymeric layer. The polymeric layer may be latex, such as PVC and polyamide. The polyamide may be produced by copolymerizing piperazine and di-acylchloride. The '060 patent discloses a membrane used as an ion selective electrode consisting of PVC, $KB(Cl-Ph)_4$ or $NaB(Ph)_4$, a plasticizer, and an ionophore for ion sensitivity.

OBJECTS AND SUMMARY OF THE INVENTION

The present invention provides a copolymer composition comprising a copolymer of piperazine and a halo-containing polymer wherein from about 0.01% to about 20% by weight, more preferably from about 0.1% to about 10% by weight, of the halo moieties therein are replaced with piperazine.

Also, the present invention provides a process of making a copolymer of an amine and a halo-containing polymer comprising reacting piperazine as the amine with a halo-containing polymer in a solvent for a time sufficient at a temperature sufficient under an inert gas blanket, whereby there is produced a copolymer of piperazine and halo-containing polymer, said copolymer being inherently conductive.

Also, the present invention provides a flexible polymeric film comprising a copolymer of piperazine and halo-containing polymer wherein from about 0.01% to about 20% by weight, more preferably from about 0.1% to about 10% by weight, of the halo moieties therein are replaced with piperazine. The film may comprise a membrane film and the membrane film may be in a biosensor. Also, the film may comprise a packaging film and the packaging film may be packaged around a static sensitive device.

Accordingly, it is an object of the invention to provide a novel copolymer of piperazine and halo-containing polymer, and a process for making said copolymer. It is a feature of the copolymer that it is inherently conductive. Thus, it is an advantage of the invention, that when the novel copolymer is made into a film, that the film is useful as a membrane film for a biosensor or as an antistatic film for packaging static sensitive devices. This conductive behavior is especially surprising since polymeric films are in general dielectrics (insulators) and require an additive to make them conductive. The preferred halo-containing polymer is polyvinyl chloride (abbreviated herein as PVC).

Some of the features, objects and the like of the invention having been stated hereinabove, other objects will become evident as the description proceeds, when taken in connection with the accompanying Laboratory Examples as best described hereinbelow.

DETAILED DESCRIPTION OF THE INVENTION

By reacting a small, highly basic amine, namely piperazine, with PVC, in order to substitute some of the chlorine moieties with piperazine moieties, an ionically conductive PVC-piperazine copolymer was made, and from the copolymer an ionically conductive flexible plastic film was made. By conductive is meant that the film should exhibit Nernstian behavior when the film is a membrane or should dissipate 5000 volts direct current in less than 2000 milliseconds when the film is a packaging film. Both Nernstian behavior and dissipation of 5000 Vdc are discussed further below. It is contemplated that besides substituting in PVC, piperazine should also substitute in any halogen containing polymer, including, but not limited to vinylidene chloride polymers and copolymers (i.e., vinylidene chloride-vinyl chloride, vinylidene chloride-methyl acrylate, or vinylidene chloride-acrylonitrile), polyvinyl fluoride, polychloroprene, and the like, and that these piperazine substituted halo-polymers should also be conductive. The replacement of halo moieties with piperazine moieties preferably is about 0.01% to about 20% by weight, more preferably about 0.1% to about 10% by weight. It is noted that halo and halogen are used interchangeably herein, and by these terms it is intended to include the members of Group VII, namely F, Cl, Br, and I.

Since the copolymers of the invention are conductive, they should be useful for various applications. One application would be as a membrane film in a biosensor. For instance, in one type of biosensor, a very thin tube is used during heart surgery. Inside the thin tube is a very thin (the size of a human hair) silver wire with a chlorodized tip. The end of the tube would have the membrane over it. The tube is inserted with the wire therein through a blood vessel and into the heart. Then, the tip of the wire is touched to one side of the membrane, and the other side of the membrane is touched to the heart to take an electrical measurement thereof. Alternatively, the wire can be inserted directly into the heart muscle as well to measure and map the ischemic regions of the heart. Another biosensor application would be to use the instant membrane as a substrate for an enzyme-based biosensor. For instance, one kind of enzyme-based biosensor is used in testing Alzheimer's patients. Alzheimer's patients form beta amyloid, and thus the biosensor would have beta amylase as an enzyme in order to test for beta amyloid. Another kind of enzyme-based biosensor would be a biosensor with an enzyme that is for testing prostate specific antigen. This type of biosensor would be useful in obtaining the baseline for prostate specific antigen in male patients in order to determine if over the years it would change from the baseline. Any such change would be indicative that the male patient could be likely to develop prostate cancer, one of the most common cancers in the male population. Biosensors are generally discussed in Buerk, *Biosensors Theory and Applications*, Technomic Publishing Co. (1993), in Meyerhoff et al., "New Anion- and Gas-Selective Potentiometric Sensors", *ACS Symposium Series* 403 *Chemical Sensors and Microinstrumentation*, Chp. 2, pp. 26–45 (Sep. 25–30, 1988), and in Cha et al., "Electrochemical Performance, Biocompatability, and Adhesion of New Polymer Matrices for Solid-State Ion Sensors", *Analytical Chemistry*, Vol. 63, No. 17, pp. 1666–1672 (Sep. 1, 1991).

Another use of the instant copolymers would be as films for battery separators since the films are not affected by sulfuric acid and batteries have sulfuric acid; these battery separators could be of different shapes.

Also, since the instant copolymers are conductive, it is contemplated that when made into a film, such as by well-known extrusion techniques, such films could be used as an antistatic plastic for packaging of static-sensitive devices such as electronic circuit boards. As is known in the art, the antistatic property is exhibited by the ability of a polymeric film to promote static charge decay, i.e., to dissipate a static charge. The test is performed according to Federal Test Method 101C, Method 4046.1, "Electrostatic Properties of Materials", which states that when 5000 volts direct current is applied to a film, 99% of the applied static charge will dissipate in less than 2000 milliseconds. Samples of plastic film are equilibrated at 15% relative humidity at about room temperature for about 24 hours prior to the test. The instant films should exhibit this behavior of dissipating the 5000 Vdc in less than 2000 milliseconds, and thus should be useful for packaging electronic circuit boards. It is noted that surprisingly the instant polymeric films are inherently conductive, whereas the polymeric films presently on the market for antistatic packaging contain some kind of additive to make the plastic antistatic, which additive, over time (the time may be two or three years or may be short, such as a few weeks) will eventually bleed and contaminate the item packaged with the antistatic film.

In the Laboratory Examples below, the reaction of piperazine and PVC took place under an inert gas blanket in methanol as the solvent, but it is contemplated that any solvent, such as methanol, ethanol, 2-butanone, and conbinations thereof, which will dissolve piperazine and/or the halo-containing polymer should work. The reaction must take place under an inert atmosphere, such as a nitrogen atmosphere or an argon atmosphere, in order to maintain the concentration of the reactants. By maintaining the concentration of the reactants is meant that it is desired that evaporation of the solvent, hydration of the piperazine and/or oxidation of the halo-containing polymer does not occur to such an undesirable extent that only very little halo-containing polymer and piperazine react to form a copolymer of halo-containing polymer and piperazine, such as PVC-piperazine copolymer. In the Laboratory Examples below, the amination of PVC with piperazine was performed under an argon blanket.

The amination was conducted at various times and temperatures as noted in the Laboratory Examples below, and after the methanol was removed, a yellow-colored powdered polymer was obtained. As the time and temperature of the reaction can vary widely, the time should be sufficient and the temperature should be sufficient so that a copolymer of halo-containing polymer and piperazine, such as PVC-piperazine copolymer, results. Preferably, the time ranges from instantaneous to about 50 days, and preferably, the temperature ranges from about 0° C. to about 75° C., more preferably from about room temperature to about 65° C. However, as discussed in more detail below, it is contemplated that the reaction could be run in the cold for a very long time.

It is believed the reaction mechanism for PVC and piperazine proceeds as follows:

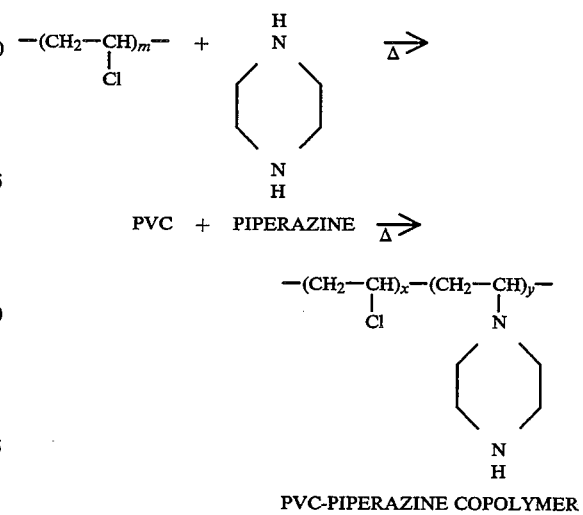

PVC-PIPERAZINE COPOLYMER and it is noted that the piperazine moiety present in the PVC-piperazine copolymer structure has one of its two N's positioned as a secondary amine, which is further discussed two paragraphs below. Also, it is believed that some

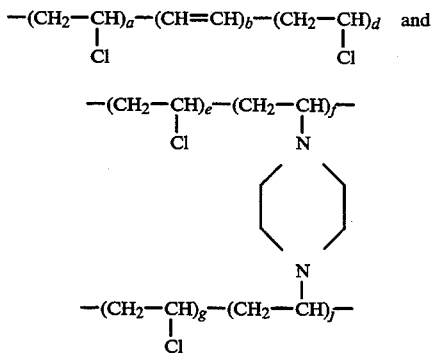

moieties also may be formed in the polymer chain, where m, x, y, a, b, d, e, f, g, and j, each is an integer designating the repeating groups in the polymer chain.

While it is not intended to be bound to any theory, it is believed that some of the moiety

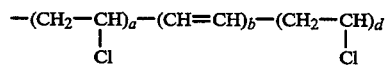

may be formed in the polymer chain because the resultant polymer has a yellow color. It is known that conjugation of alternating double bonds and single bonds in a polymer backbone carbon chain causes a yellowish to brownish chromophore effect in the resultant polymer. Also, it is known that heating a chlorine-containing polymer can cause HCl to leave, resulting in conjugation in a polymer backbone carbon chain giving the chlorine-containing polymer a yellowish to brownish color.

Also, while it is not intended to be bound to any theory, it is believed that some of the moiety

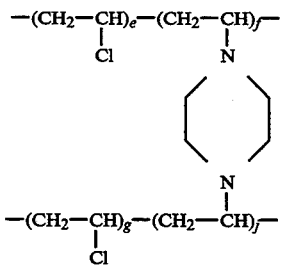

also may be formed in the polymer chain because this structure shows cross-linking via each N in the piperazine moiety. This cross-linking illustrated in the structure immediately above shows one of the N's in the piperazine moiety is not secondary, but rather both N's are tertiary. In other words, it is believed that perhaps tertiary amines do not participate in the transfer of the charge as much as the secondary amine in the piperazine moiety present in the PVC-piperazine copolymer structure illustrated further above. As described in more detail in the Laboratory Examples below, the potentiometric pH response varied in some of the resultant copolymers, and thus apparently, this variation appears to have been due to such cross-linking whereby not every piperazine moiety in polymer chain of the PVC-piperazine had one of its N's positioned as a secondary amine.

Each time the reaction to make PVC-piperazine copolymer was performed at a different time/temperature as designated in the Laboratory Examples below, the resultant was analyzed for nitrogen content, which was found to range from about 0.23 to about 1.63% by weight. More preferably the range of the nitrogen content was from about 0.5 to about 0.8% by weight for those PVC-piperazine copolymers made into membranes that in general exhibited good Nernstian behavior, which is discussed in more detail in the Laboratory Examples below. Standard methods, i.e., the combustion method or the Kjeldahl method, were used to determine the nitrogen content. In order to make membrane films as described in the Laboratory Examples below, the PVC-piperazine copolymer powder was dissolved in tetrahydrofuran (hereinafter THF). The THF also contained plasticizer (ortho-nitrophenyl-octyl ether) and potassium tetrakis para-chlorophenyl-borate (hereinafter KTpClPB). Then, the THF was evaporated off, leaving a plastic membrane film. Membranes having a thickness of about 200 microns and good flexibility were cast. Sometimes a particular PVC-piperazine copolymer made would not dissolve in the THF. Thus a membrane was not made from that particular PVC-piperazine copolymer as a solvent other than THF was not tried, and these samples are designated NS (an abbreviation for not soluble) in Table 1 below. This method of solvent casting of membranes from a THF solution is known from Craggs, Moody, and Thomas, "PVC Matrix Ion-Selective Electrodes", *J. of Chemical Education*, Vol. 51, No. 8, pp. 541–544 (August, 1974), and from Moody, Oke, and Thomas, "A Calcium-sensitive Electrode Based on a Liquid Ion Exchanger in a Poly(vinyl chloride) Matrix", *Analyst*, Vol. 95, pp. 910–918 (November, 1970).

Other methods of making a polymeric film from polymeric powder, beads, pellets and the like are well known to those of ordinary skill in the art. Some of these methods, in addition to the casting solvent evaporation method just mentioned, are spin casting, ink jet deposition, extrusion (either planar or tubular), and the like, and it is not intended to be limited thereby.

It is also believed that plastic films of PVC-piperazine copolymer could be made by applying a coating of piperazine to a sheet of PVC, and then treating that with radiation. Alternatively, the PVC sheet could be irradiated first and then the piperazine applied thereto. Either way could be done under vacuum and/or in the presence of a solvent, such as methanol. The radiation should cause the piperazine to substitute for some of the chlorine in the PVC sheet. Irradiation may be accomplished by the use of high-energy electrons, ultraviolet radiation, X-rays, gamma rays, beta particles, etc. If electrons are employed as the source of radiation, the dosage could be up to a few megarads, with higher megarads being employed when the electron volt generator is at a lower voltage. Electron beam generators, in general, operate in a range of about 150 kilovolts to about 6 megavolts.

Also, it is believed that in any of these methods for reacting the PVC with the piperazine, the reaction could take place with cold for a long time, and the substitution reaction of the piperazine replacing the chlorine should achieve greater substitution and thus the resultant PVC-piperazine copolymer should be more conductive. Such cryo-treatment would be desirable in that it would avoid the heat, which as mentioned above, is known to cause conjugation of alternating double bonds and single bonds in the polymer backbone that has the yellow color. Avoiding the conjugation should result in a colorless polymer film, which is aesthetically appealing for certain applications.

Although it is not intended to be bound to any theory, it is believed that since no mobile sites are available, that therefore the mechanism of ion transfer in the conductive PVC-piperazine copolymer films was most likely occurring by intermolecular ion hopping. Since amine sites are fixed along the backbone of the PVC molecule, over 100 carbon atoms apart, intramolecular hopping most likely is not possible. Instead, it is believed that intermolecular hopping occurs by a combination of reptation and chain flexure, as otherwise rigid PVC-piperazine molecules assume a more random conformation within their plasticized environment.

Also while it is not intended to be bound to any theory, since the presence of some quaternary nitrogen may be observed during X-ray photoelectronspectroscopy in the PVC-piperazine copolymer membranes made, it is believed that there is most likely an exchange of charged species as molecules pass near one another, cross over one another, or loop over one another forming a physical entanglement. It is further believed that these intermolecular conformations are driven by both the electromotive potential difference between reference and ion specific components and by the chemical gradient between the positively charged amine sites of the piperazine moiety and the negatively charged sites of the KTpClPB. There are likely to be other conformational factors, also, as a site that was once a low energy site becomes less favorable because of a change in the conformational energy of its parent molecule as well as its neighbors. Consequently, it is believed that when an unfilled aminated site presents itself, which should lower the local conformational energy of the membrane and satisfy electromotive potential and chemical gradient criteria, the proton hops.

The following substances were used for the synthesis of PVC-amine copolymers and films thereof described in the Laboratory Examples below. High molecular weight PVC (MW 110,000) was purchased from Polysciences. The o-nitrophenyl octyl ether (abbreviated as o-NPOE), bis(2-ethylhexyl)sebacate (also known as dioctylsebacate and abbreviated as DOS), dibutylsebacate (abbreviated as DBS) and potassium tetrakis p-chlorophenylborate (abbreviated as KTpClPB) were products of Fluka Chemie. Dioctylphthalate (abbreviated as DOP) was supplied by Aldrich Chemical Co. Epoxydized soybean oil (abbreviated as ESO) was obtained from the Solvent and Coating Materials Division of Union Carbide Corporation and subsequently purified by gel permeation chromatography (Waters, Division of Millipore) using methylene chloride as the mobile phase and a 200 angstrom Styragel preparative column of dimensions, 20 mm×1220 mm. It is noted that sometimes synthesis of a PVC-piperazine membrane film from a THF solution was repeated using a plasticizer other than o-NPOE (such as DOS, DBS, DOP or ESO) as some plasticizers are more biocompatible should the desired end use of the membrane be in a biosensor; this data is not further discussed in the Laboratory Examples.

EXAMPLES

Example I (PVC-piperazine copolymer)

As set out in Table 1 below, several PVC-piperazine copolymer samples were synthesized and made into sensor membranes which were tested for potentiometric pH response. For each synthesis, the PVC was placed in a clean, round bottom flask, containing a magnetic stirring bar. The piperazine was weighed and poured into the flask using a powder funnel. Then, pre-measured methanol was poured through the same funnel into the flask. The ratio of the methanol:piperazine:PVC was 13.8:6.9:1.0, which was 39.5 g:19.7 g:2.86 g.

A Claisen adapter was connected to the flask. In the straight arm of the adapter, another adapter, which had a gas inlet for argon and a center opening for a thermowell, was attached. A Graham condenser was attached to the curved arm of the Claisen adapter. A gas trap was attached to the top opening of the condenser. While the piperazine was dissolving, an argon blanket was allowed to flow through the system. For those samples where the reaction was allowed to continue for several days, argon was entered once or twice per day.

Heat was applied via a small heat tape that was placed into a heating mantle. The temperature was regulated via a controller that used a thermocouple placed into a thermowell. The time began when the solution reached the desired temperature for the reaction. At the end of the desired time, the controller was turned off and excess methanol was added to the reaction flask to help dilute the unreacted piperazine.

The solution was carefully decanted into a polytetrafluoroethylene filter funnel (containing a polytetrafluoroethylene filter) so that the resultant PVC-piperazine copolymer remained in the flask. The copolymer was washed with methanol, and again the solvent was removed by decanting. The copolymer was then washed with deionized water twice and then washed with 0.1M NaOH once. Then, the copolymer was washed again with distilled water and the pH was checked with pHydrion paper. This washing with distilled water was continued until the pH was down to 6 or 7. The copolymer was then washed with methanol twice more. Then, the copolymer was washed out of the flask and into the funnel. The filtrate was washed once more with methanol and then vaccuum was allowed to remove any remaining solvent. The powdered PVC-piperazine copoylmer was placed in a vaccuum at room temperature overnight.

Thin membrane films were made from the polymeric powder by making a solution of 33.0% of the PVC-piperazine copolymer powder, 66.0% of o-nitrophenyl octyl ether as plasticizer, and 1.0% KTpClPB (the three ingredients weighing approximately 300 mg) in 4 ml of THF as the solvent. The THF solution was poured into a short glass ring that was sitting on a glass plate so that the THF would evaporate off, leaving the membrane film which was then peeled off the glass plate. Membranes were cut into disks of approximately 10 mm in diameter for testing. It is noted that these membranes were ionophore-free.

Then, using known techniques, a disk of each membrane was tested for potentiometric pH response, i.e., Nernstian behavior. This was done by placing the membrane disk at the end of an electrode body, and then submerging that electrode and a reference electrode into a buffered solution so that the pH was constant, and then determining the electromotive force across those two electrodes at that pH. Various buffers were used for the different pH's, and these were various citrate-borate buffers or various Tris buffers. The potential was measured as a function of pH at 22.5° C. with an Orion Expandable Ion Analyzer (Model EA 920) connected to an Orion Electrode Switch (Model 607) and compared with the outcomes of Emf across a glass electrode and the reference electrode. The method followed for measuring Emf to determine Nernstian behavior was as described in Buerk, "Electrochemical Transducers in Biology and Medicine", *Biosensors Theory and Applications*, Chp. 3, pp. 39-45, Technomic Publishing Co. (1993).

Most membranes exhibited an Emf of about 300 volts at a pH of 2 to an Emf of about −250 volts or −300 volts at a pH of about 12, so that a voltage drop was exhibited over a range of approximately 10 pH units, i.e., from pH=2 to pH=12. The slope for each membrane for this testing of the Emf values at the different pH values was calculated. Like the slope of the glass electrode, the slope of most of the PVC-piperazine copolymer membranes was essentially Nernstian (about −59 millivolts/pH to about −60 millivolts/pH) over pH values that ranged from about 4 to 12. It is noted that sample 73 was measured repeatedly over 60 days, and still showed Nernstian behavior on day 60.

Also, using standard analytical methods of combustion or Kjeldahl to determine the percent nitrogen, the amount of nitrogen in the PVC-piperazine copolymer was determined. These results are summarized in Table 1 below:

TABLE 1

| Sample # | Temperature (°C.) | Time | % Nitrogen | | pH Range | -Slope |
|---|---|---|---|---|---|---|
| 42 | 64 | 1 d | 0.91 | (NS) | — | — |
| 43 | 64 | 14.5 h | 1.63 | (NS) | — | — |
| 44 | 64 | 8 h | 1.07 | (NS) | — | — |
| 45 | 64 | 4 h | 0.56 | | 5-12 | 54.6 |
| 46 | 25 | 11 d | 0.23 | | 7-12 | about 0 |
| 47 | 35 | 7 d | 0.62 | | 4-11 | 58.0 |
| 48 | 45 | 1 d | 0.74 | | 4-10 | 54.2 |
| 58 | 25 | 14 d | 0.30 | | 2-6 | 26.1 |
| 59 | 25 | 31 d | 0.56 | | 4-11 | 57.8 |
| 60 | 35 | 7 d | 0.45 | | 4-10 | 48.0 |
| 61 | 35 | 7 d | 0.83 | (NS) | — | — |
| 62 | 35 | 7 d | 0.39 | | 4-11 | 26.1 |
| 65 | 35 | 10 d | 0.66 | | 5-12 | 57.5 |
| 66 | 40 | 6 d | 0.84 | | 4-11 | 56.9 |
| 71 | 35 | 7 d | 0.50 | | 4-12 | 58.8 |
| 72 | 35 | 10 d | 0.67 | | 4-10 | 44.7 |
| 73 | 35 | 10 d | 0.72 | | 5-12 | 58.9 |
| 74 | 35 | 7 d | 0.77 | | 5-12 | 59.4 |
| 75 | 35 | 7 d | 0.75 | (NS) | — | — |
| 76 | 35 | 7 d | 0.53 | | 5-12 | 60.8 |
| 78 | 50 | 1 d | 0.64 | | 5-11 | 60.6 |
| 79 | 50 | 16 h | 0.89 | | 5-11 | 60.9 |
| 80 | 50 | 4 h | 0.64 | | 5-11 | 59.5 |
| 81 | 50 | 16 h | 0.60 | | 5-11 | 59.8 |
| 82 | 50 | 8 h | 0.57 | | 5-11 | 58.6 |
| 83 | 45 | 1 d | 0.55 | | 5-11 | 60.1 |
| 84 | 45 | 2 d | 0.73 | | 5-11 | 60.8 |
| 85 | 45 | 3 d | 0.60 | | 5-12 | 61.8 |
| 86 | 40 | 3 d | 0.62 | | 5-11 | 60.7 |
| 87 | 30 | 7 d | 0.55 | | 5-11 | 60.3 |
| 88 | 40 | 4 d | 0.65 | | 5-12 | 61.6 |
| 89 | 30 | 14 d | 0.44 | | 4-12 | 57.1 |
| 90 | 30 | 10 d | 0.58 | | 5-12 | 58.1 |
| 91 | 25 | 49 d | 0.88 | (NS) | — | — |
| 92 | 35 | 20 d | 0.78 | (NS) | — | — |
| 93 | 45 | 4 d | 0.76 | | 4-12 | 59.7 |
| 94 | 50 | 3 d | 1.05 | (NS) | — | — |
| 95 | 50 | 5 d | 1.29 | (NS) | — | — |

TABLE 1-continued

| Sample # | Temperature (°C.) | Time | % Nitrogen | | pH Range | -Slope |
|---|---|---|---|---|---|---|
| 96 | 50 | 7 h | 0.66 | | 4-12 | 59.2 |
| 97 | 35 | 4 d | 0.50 | | 4-12 | 58.2 |
| 98 | 40 | 2 d | 0.60 | | 4-12 | 59.6 |
| 99 | 45 | 15 h | 0.58 | | 5-12 | 58.2 |
| 100 | 45 | 6 d | 1.22 | (NS) | — | — |
| 101 | 30 | 6 d | 0.37 | | 3-12 | 19.0 |
| 102A | 35 | 10 d | 0.87 | | 5-12 | 58.6 |
| 102B | 35 | 10 d | 0.74 | | 5-12 | 58.5 |
| 103 | 35 | 10 d | 0.80 | | 4-12 | 58.7 |
| 104 | 30 | 20 d | 0.60 | | 4-12 | 56.5 |
| 105 | 45 | 7 h | 0.57 | | 3-12 | 21.5 |
| 106 | 45 | 5 h | 0.46 | | 3-12 | 19.0 |
| 107 | 30 | 4 d | 0.31 | | 2-6 | 24.0 |

NS = not soluble. In other words, the particular PVC-piperazine copolymer made was not soluble in the solvent THF. Thus, a membrane film could not be made via evaporation from a THF solution. Other solvents were not tried, so no membrane film was made for these particular PVC-piperazine copolymers.
d = days; h = hours.

While it is not intended to be bound to any theory, it is believed that samples 46, 58, 62, 101, 105, 106, and 107 did not exhibit Nernstian behavior because the temperature was too low and the time was too short, i.e., the lower the temperature is, then the longer the time should be.

Example II (PVDC-piperazine copolymer)

Additionally, following essentially the same procedure set out in Example I, piperazine was reacted with some chlorine-containing polymers other than PVC at various temperatures. The other chlorine-containing polymers used were copolymers of polyvinylidene chloride (commonly known as Saran, which has lost its trademark status and become generic in the United States). In particular, the three copolymers of polyvinylidene chloride that were used were vinylidene chloride/acrylonitrile copolymer (Saran F-310), vinylidene chloride/vinyl chloride copolymer (Saran 313), and vinylidene chloride/vinyl chloride copolymer (Saran 866). At each temperature tried, the reaction occurred so rapidly as to be considered spontaneous, as the reaction was even continuing while the product was being washed. At temperatures above 50° C., the product quickly turned black in less than one hour.

Example III (First Comparative Example)

Besides the synthesis of PVC-piperazine copolymer and PVDC-piperazine copolymer, synthesized were various other formulations of substituted PVC employing other amines. These other amines were 1,2-diaminoethane, 1,2-diaminopropane, 1,3-diaminopropane, 1,4-diaminobutane, 1,6-diaminohexane, 1,7-diaminoheptane, 1,8-diaminooctane, 1,12-diaminododecane, trans-1,4-diaminocyclohexane, 1,8-diamino-para-menthane, and 1,4-bis(3-aminopropyl)piperazine. This was done because it was desired to see if a membrane cast by evaporation of a THF solution thereof, wherein the membrane was PVC aminated with some other amine, would exhibit a potentiometric pH response (i.e., Nernstian behavior). The amination reaction proceeded, but the resultant membrane of PVC aminated with another amine did not exhibit Nernstian behavior, except that the membrane of copolymer of 1,8-diaminooctane and PVC exhibited Nernstian behavior but only at a basic pH greater than 7. Thus, it is noted that the pH potentiometric response, as set out in the two Ma et al. articles discussed above in the beginning of the "Background of the Invention" section, could not be repeated.

Example IV (Second Comparative Example)

Strength tests were performed on PVC films wherein the PVC of each film was of a different molecular weight. Each PVC membrane was made by evaporation of a THF solution containing dissolved therein the powdered polymer and dioctylsebacate as plasticizer, but no KTpClPB. After the THF was evaporated off, a thin flexible polymeric membrane film resulted. After hydration of the membrane for 24 hours in a pH 7 buffer solution, puncture tests were performed on the membrane using an Instron machine, and film thicknesses were measured with a Dektak profilometer (supplied by DuPont MicroElectronics). It was noted that as the molecular weight of the PVC used in the membrane increased, then the force at rupture of the membrane also increased. Thus, higher molecular weight PVC has better mechanical properties, i.e., better puncture resistance.

Thus, in the instant invention it would be expected that using higher molecular weight PVC for the amination reaction with piperazine would result in higher molecular weight PVC-piperazine copolymer, which resultant should also have better mechanical properties, i.e., better puncture resistance. The better puncture resistance is desirable in connection with the heart biosensor mentioned above, since during the heart test, if the silver wire went through the PVC-piperazine copolymer membrane at the end of the tube, the silver wire would be directly touching the heart and a short circuit would result.

It will be understood that various details of the invention may be changed without departing from the scope of the invention. Furthermore, the foregoing description is for the purpose of illustration only, and not for the purpose of limitation—the invention being defined by the claims as follows.

What is claimed is:

1. A copolymer composition comprising a copolymer of piperazine and a halo-containing polymer wherein from about 0.01% to about 20% by weight of the halo moieties therein are replaced with piperazine.

2. A copolymer composition comprising a copolymer of piperazine and a halo-containing polymer wherein from about 0.01% to about 20% by weight of the halo moieties therein are replaced with piperazine, wherein the halo-containing polymer is selected from the group consisting of polyvinyl chloride, polyvinyl fluoride, polyvinylidene chloride copolymers, and polychloroprene.

3. A copolymer composition comprising a copolymer of piperazine and a halo-containing polymer wherein from about 0.01% to about 20% by weight of the halo moieties therein are replaced with piperazine, wherein the halo-containing copolymer is polyvinyl chloride whereby the resultant copolymer has repeating units of the formula $-CHQ-CH_2-$, wherein Q is selected from the group consisting of Cl and piperazinyl, and wherein from about 0.1% to about 10% by weight of Q is piperazinyl.

4. A flexible polymeric film comprising a copolymer of piperazine and a halo-containing polymer wherein from about 0.01% to about 20% by weight of the halo moieties therein are replaced with piperazine.

5. A flexible polymeric film comprising a copolymer of piperazine and a halo-containing polymer wherein from about 0.01% to about 20% by weight of the halo moieties therein are replaced with piperazine, wherein the halo-containing polymer is selected from the group consisting of polyvinyl chloride, polyvinyl fluoride, polyvinylidene chloride copolymers, and polychloroprene.

6. A flexible polymeric film comprising a copolymer of piperazine and a halo-containing polymer wherein from about 0.01% to about 20% by weight of the halo moieties therein are replaced with piperazine, wherein the halo-containing copolymer is polyvinyl chloride whereby the resultant copolymer has repeating units of the formula $-CHQ-CH_2-$, wherein Q is selected from the group consisting of Cl and piperazinyl, and wherein from about 0.1% to about 10% by weight of Q is piperazinyl.

7. The film of claim 4 wherein said film comprises a membrane.

8. The film of claim 4 wherein said film comprises a packaging film.

9. The film of claim 4 wherein said film is inherently conductive.

10. The film of claim 5 wherein said film comprises a membrane.

11. The film of claim 5 wherein said film comprises a packaging film.

12. The film of claim 5 wherein said film is inherently conductive.

* * * * *

UNITED STATES PATENT AND TRADEMARK OFFICE
CERTIFICATE OF CORRECTION

PATENT NO. : 5,403,895
DATED : April 4, 1995
INVENTOR(S) : Robert P. Kusy et al.

It is certified that error appears in the above-identified patent and that said Letters Patent is hereby corrected as shown below:

At Line 3 of the "ABSTRACT" in Item [57] on the front page, between "about" and "by weight" insert -- 20% --.

Column 8, Line 50, change "vaccuum" instead to read as -- vacuum --.

Signed and Sealed this

Eleventh Day of July, 1995

Attest:

BRUCE LEHMAN

*Attesting Officer*  *Commissioner of Patents and Trademarks*